United States Patent [19]

Davis et al.

[11] Patent Number: 5,307,697
[45] Date of Patent: May 3, 1994

[54] CONTINUOUS, AUTOMATED, MULTI-STREAM SAMPLE COLLECTION AND ANALYSIS

[75] Inventors: H. Forbes Davis; Anthony J. Freed, Jr., both of Tallevast, Fla.

[73] Assignee: Davis Water & Waste Industries, Inc., Tallevast, Fla.

[21] Appl. No.: 883,032

[22] Filed: May 14, 1992

[51] Int. Cl.[5] ................................................ G01N 1/14
[52] U.S. Cl. ............................. 73/864.81; 73/864.34
[58] Field of Search ............ 73/863.01, 863.23, 863.24, 73/863.33, 863.83, 864.34, 864.31, 864.81

[56] References Cited

U.S. PATENT DOCUMENTS

| | | | |
|---|---|---|---|
| 3,464,272 | 9/1969 | Griffith et al. | 73/863.33 |
| 4,056,982 | 11/1977 | Jones | 73/864.34 |
| 4,090,392 | 5/1978 | Smith et al. | 73/863.23 |
| 4,155,247 | 5/1979 | Kaczmarek et al. | 73/863.23 |
| 4,198,862 | 4/1980 | Rubin | 73/863.83 |
| 4,250,752 | 2/1981 | Ongley | 73/863.33 |
| 4,341,124 | 7/1982 | Rodgers et al. | 73/863.23 |
| 4,432,250 | 2/1984 | Albrecht et al. | 73/863.83 |
| 4,727,758 | 3/1988 | Murdock | 73/863.24 |

FOREIGN PATENT DOCUMENTS

1360346 7/1974 United Kingdom ............ 73/863.83

Primary Examiner—Robert Raevis
Attorney, Agent, or Firm—Nixon & Vanderhye

[57] ABSTRACT

In the treatment of sewage, fresh, representative samples are continuously collected and analyzed at a number of different points in a sewage treatment reservoir. A submersible grinder pump is connected by a sample supply conduit to a continuous flow through filter, and ground sewage slurry is delivered at high velocity through the filter so that it scours the internal surfaces of the filter. The sewage slurry is continuously returned to the treatment reservoir, and filtrate continuously passes through a rotameter to a transparent sample collection reservoir. Discharge from the sample reservoir is controlled by a solenoid operated valve, and a continuous overflow waste return conduit allows return of the filtrate to the treatment reservoir if the solenoid valve is closed. A computer controls operation of the solenoid valves and one or more analyzers for analyzing filtrate qualities (such as alkalinity). The solenoid controlled valves are connected to the analyzer through a manifold.

20 Claims, 2 Drawing Sheets

5,307,697

CONTINUOUS, AUTOMATED, MULTI-STREAM SAMPLE COLLECTION AND ANALYSIS

BACKGROUND AND SUMMARY OF THE INVENTION

It is very desirable to be able to collect samples of sewage from a wide variety of different sewage treatment reservoirs to determine whether the sewage is being treated properly, has the desired qualities, etc. This is true with respect to a wide variety of sewage parameters, but particularly for determining alkalinity, such as described in U.S. Pat. No. 5,094,752, the disclosure of which is hereby incorporated by reference herein.

There are a number of commercially available systems that allow samples to be collected and analyzed, however a major drawback associated with such systems is low dependability and high maintenance. Typical sample collection and analysis systems requiring servicing as often as hourly or daily, and often do not give the user confidence in the reliability of the quality and quantity of the samples, making suspect the results of the analytical procedures that are performed.

According to the present invention, a sample collection and analytical system, and a method of collecting and analyzing sewage samples from a sewage treatment reservoir, are provided which greatly enhance the dependability, reduce the maintenance, and increase confidence in the quality and quantity of sample analysis, as compared to the prior art. Utilizing the present invention, approximately a 30 day service schedule may be expected, with high quality results throughout the entire between-service times.

According to the present invention, the sewage slurry, which often has stringy material in it that will reconstitute itself unless shredded, is acted upon by a grinder pump. The grinder pump breaks down the rags, plastics, strings, or other organic solids into fine pieces, preventing plugging of the system. The ground up sewage slurry is then passed by the grinder pump with a high velocity through a filter assembly, the high velocity flow producing a scouring effect on the inner filter walls thus greatly reducing cleaning and maintenance. The filtrate is transferred in a continuous flow through a black (to prevent algae growth) conduit to a rotameter, to a transparent sample collection reservoir, and ultimately through a solenoid controlled valve to an analyzer. The sample collection reservoir has a continuous overflow waste return means associated with it for returning overflowing filtrate to the sewage treatment reservoir. Continuous overflow ensures the constant availability of a fresh representative sample for the analyzer.

A plurality of the assemblies described above are connected together to a single analyzer, or to multiple analyzers. The solenoid valves are connected through a manifold to the analyzer, and a computer controls the analyzer and the solenoid controlled valves, and receives data from the analyzer. The analyzer may analyze any quality or qualities of the filtrate, such as alkalinity.

The method of the invention comprises collecting and analyzing sewage samples from sewage treatment reservoirs, comprising the steps of automatically: (a) At a plurality of different points in a sewage treatment reservoir, grinding up sewage solids, including stringy material, to prevent clogging of sewage transporting conduits. (b) Passing the ground sewage solids in a water slurry through a flow through filter having interior filter surfaces at such a velocity and volume as to scour the interior filter surfaces, while producing filtrate. (c) Returning the sewage slurry from the filters to the sewage treatment reservoir. And, (d) analyzing filtrate from the filter to determine properties thereof. Step (b) is preferably practiced by passing the slurry at about 35 gallons per minute through an approximately one inch internal diameter filter, which ensures the scouring action.

It is the primary object of the present invention to provide for the high dependability and low maintenance collection and analysis of high quality, representative samples associated with a sewage treatment reservoir. This and other objects of the invention will become clear from an inspection of the detailed description of the invention, and from the appended claims.

DETAILED DESCRIPTION OF THE DRAWINGS

Figure 1:
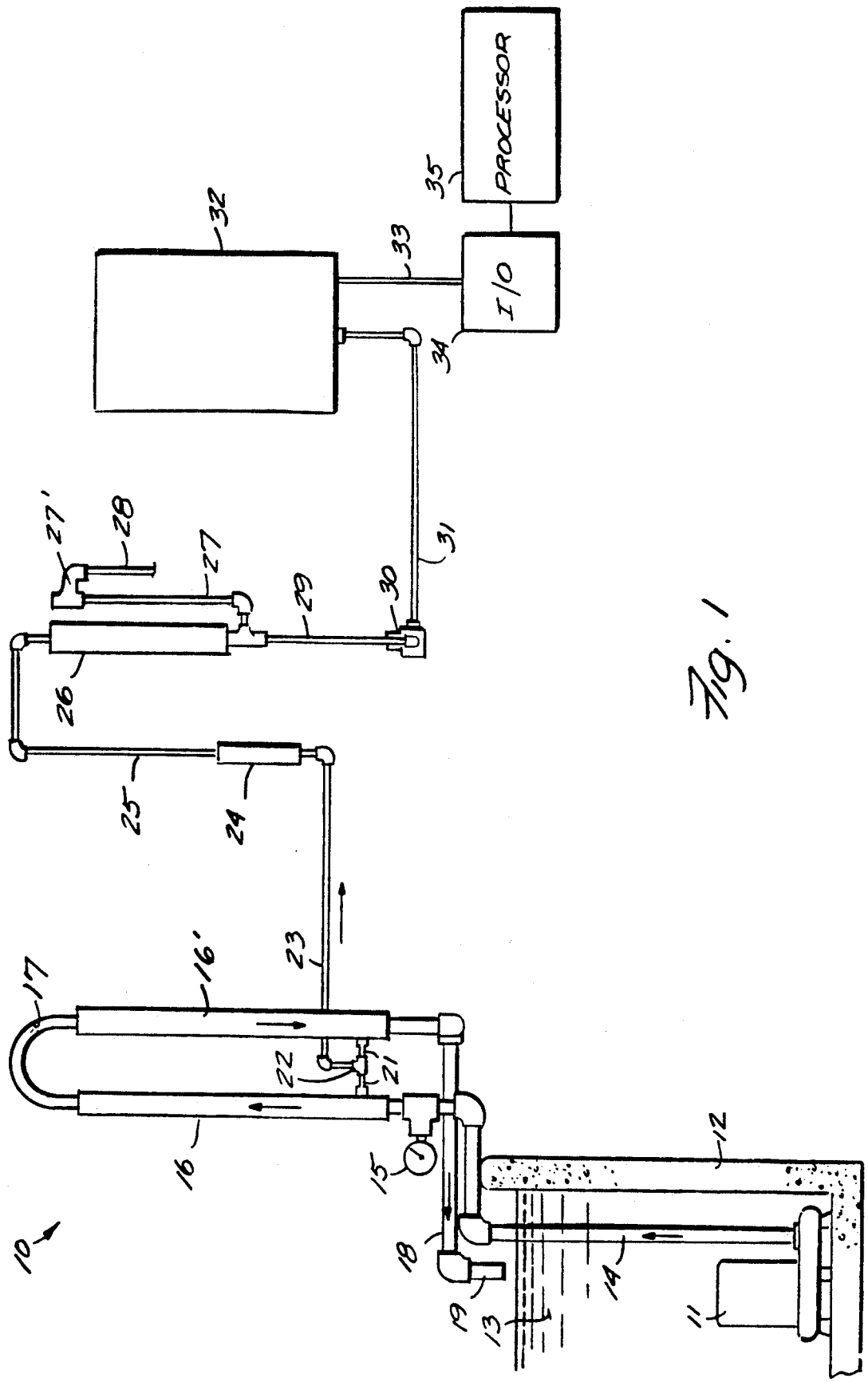
FIG. 1 is a schematic side view showing one set of apparatus in the sample collection and analytical system according to the invention.

One exemplary set of apparatus for use in an exemplary system according to the present invention is shown generally by reference numeral 10 in FIG. 1. One of the most important elements of the system 10 is a grinder pump 11 which is mounted in a sewage treatment reservoir 12 below the level of sewage 13 therein (i.e. a submersible). The grinder pump 11 must be capable of grinding a medium containing solids up to a three percent concentration, including rags, plastics, strings, and other material that will reconstitute itself unless it is shredded, as well as other organic solids. The grinding action of the pump 11 cuts and shreds the rags and other solids into fine pieces, preventing plugging of the system downstream. One exemplary commercially available grinder pump 11 that is utilizable in the present invention is an ABS Grinder Pump, Model Piranah-E2.5, with a 2.5 horsepower electric motor, 3400–3600 rpm, and a capacity of 35 gallons per minute at 30 psi. Such a pump 11 is manufactured by ABS Pumps, Inc. of Meriden, Conn.

The submersed grinder pump 11 is connected by a sample supply conduit 14 through a pressure gauge 15 to a filter assembly comprising first and second flow through filter tubes 16, 16' which may extend a vertical, horizontal, or other common plane, and in generally opposite directions and are connected together by a U-shaped conduit 17.

The pressure gauge 15 is a standard 6–60 psi pressure gauge with a gauge protector to indicate the inlet pressure to the filter tubes 16', 16.

The filters 16, 16' are used to filter mixed liquor solids from a solids stream (slurry) in a concentration of 10 parts per million up to a concentration of 30,000 parts per million. The filters 16, 16' preferably are about one inch internal diameter ultra-filter tubes connected in series, as illustrated in FIG. 1, with the filters having a pore size of about 0.01 micron, in order to provide a clear high quality sample. The high quality of the sample ensures long maintenance free runs for the analyzer utilizable with the system. The filters 16, 16' are capable of producing up to 300 ml/min. of fresh filtered sample.

When the pump 11 delivers slurry through the filter tubes 16, 16' at about 35 gpm, a scouring action is provided, cleaning the internal surfaces of the filter tubes 16, 16' and ensuring long periods between maintenance.

The vast majority of the slurry flowing through the filter tubes 16, 16' of course passes completely through them (all except for the relatively small amount of filtrate), and preferably is returned to the sewage treatment reservoir 12 by the horizontally extending conduit 18 with a downwardly directed vertical termination 19. The filtrate from the tubes 16, 16' passes through filtrate collection tubes 21 adjacent the bottoms of the tubes 16, 16', then through T and elbow connectors 22 to the filter transfer means 23 which preferably comprises a black conduit. The black conduit 23 is provided in order to prevent passage of sunlight therethrough, which would occur if it were clear tubing or almost any other color besides black. This minimizes algae growth, and thus also extends the life of the system 10 between maintenance intervals. The conduit 23 preferably is polyethylene, and has an external diameter of about ⅜ inch. Also, some sort of color coding (such as tags, stripes, etc.) may be associated therewith since a plurality of the systems 10 will be utilized with any given reservoir 12.

The tubing 23 transmits the filtrate sample to a flow meter (rotameter) 24, which typically has a 0-200 ml/min. rate indicating ability. Thus the filtrate flow rate from the filter tubes 16, 16' is determined.

A conduit 25 connects the flow meter 24 to a sample collection reservoir 26 which preferably is constructed of clear acrylic or like plastic for quick visual reference as to quantity and quality of the sample. Since a plurality of reservoirs 26 will be associated with a particular analyzer, it is desirable to allow continuous overflow of filtrate from the reservoir 26 once it fills up, and to return that to the treatment reservoir 12. Continuous flow ensures a continuous fresh sample to the downstream analyzer (32). Continuous overflow is preferably accomplished utilizing overflow waste return means comprising an upstanding leg 27 which is connected from adjacent the bottom of the reservoir 26 to a point 27' substantially even with the top of the reservoir 26; and a conduit 28 extending from point 27' back to the reservoir 12. The conduit 28 may be flexible tubing.

The sample collection reservoir 26 is connected to a valve means 30 by a conduit 29. The valve means 30 preferably comprises a solenoid operated valve such as a 12 VDC valve with a ⅜ inch inlet and a manifolded ¼ inch outlet. The electrical source for the valve 30 may be provided by a panel associated with the manifold, the manifold being shown generally by reference numeral 31 in FIGS. 1 and 2. A quick connect electrical plug and an LED indicator light may be provided for the valve 30, which is controlled by a computer control as will be hereinafter described.

The manifold 31 output is to an analyzing means, such as one or more analyzers 32, for analyzing one or more qualities of the filtrate. For example the analyzer 32 may be an alkalinity analyzer which is used to perform continuous alkalinity titrations. Such an analyzer 32 accepts a digital signal from a central control processor 35 through an input/output center 34 and cabling 33. A microprocessor is provided in the analyzer 32 which controls various steps necessary to perform a titration. When titration is completed, the analyzer 32 sends a digital signal through the I/O 34 which is detected by the processor 35 to provide a new alkalinity value. While a computer controlled alkalinity analyzer 32 is illustrated and described, it should be understood that any type of analytical method or instrumentation may be utilized associated with the mechanical components of the apparatus 10 described above.

The I/O center 34 handles the electronic communications through an RS-422 serial data highway. It is capable of accepting any combination of (either input or output) 12-bit optically isolated analog or digital signals. Typical examples of the types of communications handled by the I/O Center 34 include: digital output to the solenoid valves 30 where the processor 35 sends a signal via the RS-422 serial line 33 to the digital brainboard in the I/O Center 34 which then actuates the appropriate digital output module, sending 12 VDC current to the designated solenoid valve 30; data acquisition conducted through a request by the processor 35 for an updated reading from a particular analyzer or other sensor source, the analog brainboard in the I/O Center 34 reads the 4–20 mA signal generated by the sensor from the appropriate analog input module and communicates this value through the RS-422 serial link to the processor 35; and variable speed automated equipment control is accomplished through an analog output module connected to the control center of the equipment.

When the processor 35 determines that the speed of a particular piece of equipment, such as a blower, should be changed based on the data acquired by the system, the processor 35 communicates this change to the I/O Center 34 and the analog brainboard changes the output (either voltage or current) of the appropriate analog output module and this new output value is detected by the control center of the equipment and its speed is then changed accordingly. Automated equipment controls can also be accomplished through digital outputs when it is desired to simply start or stop equipment. This function is usually performed through relays in the motor control center of the equipment and digital output modules in the I/O Center 34.

The central control processor 35 configuration will vary depending upon application. In general the unit 35 is responsible for controlling a sequencing of the solenoid valves 30 and coordinating this activity with the functions performed by the analyzer 32 and other data generating equipment (if present). These functions may include data acquisition, display and storage, data manipulation, and output controls to automate equipment based on data gathered by the system. In the alkalinity analysis preferred embodiment, a standard IBM compatible 386SX personal computer is utilized, containing proprietary software of Davis Water & Waste Industries, Inc. of Tallevast, Fla. Other applications may require more sophisticated equipment, such as a main frame computer or similar high end equipment, or some applications may only require a simple programmable logic controller. The details of the analyzer 32 and its controls are not part of this invention.

Figure 2:
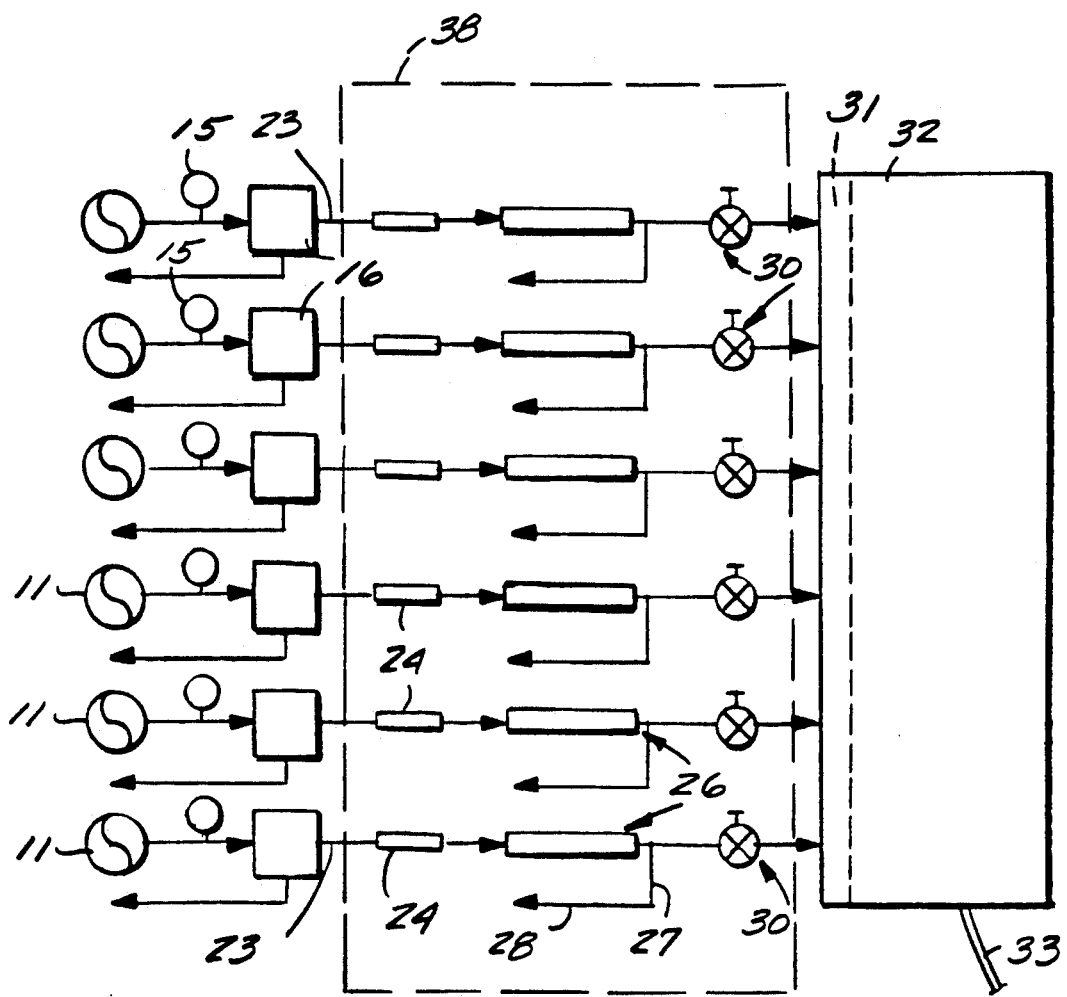
FIG. 2 a schematic illustrating a plurality of sets of apparatus of FIG. 1 connected up to a common analyzer to provide an exemplary system according to the invention.

FIG. 2 illustrates the connections of a plurality of the systems 10 to a single analyzer 32. Also illustrated in FIG. 2, in dotted line by reference 38, is a multi-stream sequencer unit housing which may be utilized to contain all of the flow meters 24, reservoirs 26, and valves 30. For instance in a typical example in which six different grinder pumps 11 are utilized spaced widely within the reservoir 12 for obtaining six different samples at different locations, the housing 38 may be a fiberglass enclosure of approximate dimensions of 48 inches by 30 inches by 10 inches, with a sloping false bottom that directs all sample spillage to an integral one inch drain. As earlier described, the conduits 23 leading into the housing 38 may be color coded for easy identification.

Utilizing the apparatus heretofore described, it will be apparent that according to the present invention collecting and analyzing of sewage samples from a sewage treatment reservoir 12 is performed automatically. At a plurality of different points in the reservoir 12 sewage solids are ground up by grinder pumps 11, including any stringy material, the grinding action preventing clogging of sewage transporting conduits downstream of the pumps 11. The ground sewage slurry is continuously passed through a flow through filter 16, 16' having interior filter surfaces, at such a velocity and volume (e.g. 35 gpm through a one inch internal diameter filter) so as to scour the interior filter surfaces, while producing filtrate. The sewage slurry is continuously returned from the filter 16, 16' through the conduits 18, 19 to the reservoir 12. The filtrate passes through black conduits 23 to the flow meters 24, and transparent reservoirs 26, and the processor 35 controls the valves 30 to determine which of the sample collection point filtrates will be fed to analyzer 32 at any one time. In a particular reservoir 26 does not have the valve 30 associated therewith opened, any overflowing filtrate will pass through conduits 27, 28 back to the reservoir 12. The analyzer 32, in cooperation with the processor 35, will analyze the filtrate to determine its properties (e.g. alkalinity).

While the invention has been herein shown and described in what is presently conceived to be the most practical and preferred embodiment it will be apparent to those of ordinary skill in the art that many modifications may be made thereof within the scope of the invention, which scope is to be accorded the broadest interpretation of the appended claims so as to encompass all equivalent structures and methods.

What is claimed is:

1. A sample collection and analytical system for use with a sewage treatment facility, comprising:
   (a) a submersible grinder pump;
   (b) a continuous sample supply conduit operatively connected to said grinder pump;
   (c) a continuous flow through filter assembly connected to said sample supply conduit;
   (d) filtrate transfer means connected to said flow through filter assembly for removing filtrate on a continuous basis therefrom;
   (e) a filtrate sample collection reservoir;
   (f) valve means connected to said collection reservoir for allowing of preventing flow of fresh, representative filtrate said reservoir therethrough; and
   (g) analyzing means for analyzing the filtrate flowing through said valve means.

2. A system as recited in claim 1 comprising a plurality of elements (a)–(f) operatively connected to said element (g), said plurality of valve means (f) connected to said element (g) through a manifold.

3. A system as recited in claim 2 wherein said pumps are mounted in a sewage treatment reservoir at spaced locations therein, and wherein each of said filter assemblies is mounted outside said sewage treatment reservoir; and further comprising a waste return conduit operatively connected to each of said filter assemblies and continuously returning sewage from each of said filter assemblies to said reservoir.

4. A system as recited in claim 3 further comprising a flow meter connected to each filtrate transfer means between said filter assembly and said sample reservoir.

5. A system as recited in claim 4 wherein said filtrate transfer means comprises a substantially black conduit.

6. A system as recited in claim 5 wherein said substantially black conduit has an external diameter of about $\frac{3}{8}$ inch.

7. A system as recited in claim 5 further comprising color coding associated with each of said substantially black conduits.

8. A system as recited in claim 3 further comprising a pressure gauge disposed in each of said sample supply conduits at the beginning of each of said filter assemblies.

9. A system as recited in claim 8 wherein each filter assembly comprises first and second series connected ultra filter tubes circular in cross section.

10. A system as recited in claim 9 wherein said filter tubes extend in a common plane and generally opposite directions.

11. A system as recited in claim 2 further comprising computer control means for controlling operation of said analyzing means and each of said valve means.

12. A system as recited in claim 11 wherein said valve means are solenoid operated valve means.

13. A system as recited in claim 2 wherein said pumps are mounted in a sewage treatment reservoir, and further comprising a continuous overflow waste return means associated with each sample collection reservoir, and connected from the sample collection reservoir to said sewage treatment reservoir.

14. A system as recited in claim 13 wherein said continuous overflow waste return means comprising an upstanding leg extending from adjacent the bottom of said sample reservoir to a point substantially even with said top of said reservoir, and a conduit extending from said point to said sewage treatment reservoir.

15. A system as recited in claim 2 wherein said analyzing means comprises an alkalinity analyzer.

16. A system as recited in claim 1 wherein said sample reservoir is of transparent material.

17. A system as recited in claim 1 wherein said grinder pump comprises means for continuously delivering a sufficient volume of a slurry of ground solids in water, and at a sufficient velocity, so as to scour said filter assembly to prevent plugging thereof.

18. A sample collection and analytical system for use with a sewage treatment facility, comprising:
   (a) a submersible grinder pump disposed in a sewage treatment reservoir;
   (b) a sample supply conduit operatively connected to said grinder pump;
   (c) a continuous flow through filter assembly connected to said sample supply conduit, comprising first and second series connected filter tubes, extending in a common plane;
   (d) filtrate transfer means connected to said flow through filter assembly for removing filtrate therefrom on a continuous basis;
   (e) analyzing means for analyzing the filtrate flowing from said filtrate transfer means;
   (f) solenoid valve means for allowing or preventing flow of filtrate from said filtrate transfer means to said analyzing means; and (g) computer control means for controlling said analyzing means and said solenoid valve means.

19. A method of continuously collecting and analyzing sewage samples from a sewage treatment reservoir, comprising the steps of automatically:
  (a) at a plurality of different points in a sewage treatment reservoir, continuously grinding up sewage solids, including stringy material, to prevent clogging of sewage transporting conduits;
  (b) continuously passing the ground sewage solids in a water slurry through a flow through filter having interior filter surfaces at such a velocity and volume as to scour the interior filter surfaces, while producing filtrate;
  (c) continuously returning the sewage slurry from the filters to the sewage treatment reservoir; and
  (d) analyzing filtrate from the filter to determine properties thereof.

20. A method as recited in claim 19 wherein step (b) is practiced by passing the slurry at about 35 gpm through an approximately one inch internal diameter filter.

* * * * *